(12) United States Patent
Bennett

(10) Patent No.: US 11,604,204 B2
(45) Date of Patent: Mar. 14, 2023

(54) SELF-CONTAINED SYSTEMS AND METHODS FOR CONTROLLED DISPENSING OF HAZARDOUS FLUID

(71) Applicant: University of Washington, Seattle, WA (US)

(72) Inventor: Steven Bennett, Seattle, WA (US)

(73) Assignee: University of Washington, Seattle, WA (US)

( * ) Notice: Subject to any disclaimer, the term of this patent is extended or adjusted under 35 U.S.C. 154(b) by 321 days.

(21) Appl. No.: 16/887,148

(22) Filed: May 29, 2020

(65) Prior Publication Data
US 2020/0378998 A1 Dec. 3, 2020

Related U.S. Application Data

(60) Provisional application No. 62/856,382, filed on Jun. 3, 2019.

(51) Int. Cl.
*G01N 35/10* (2006.01)
*G01N 1/14* (2006.01)
(Continued)

(52) U.S. Cl.
CPC ............ *G01N 35/1016* (2013.01); *A61J 1/20* (2013.01); *A61J 1/2096* (2013.01); *A61J 1/22* (2013.01);
(Continued)

(58) Field of Classification Search
CPC .. G01N 35/1016; G01N 1/14; G01N 35/1009; G01N 2001/002;
(Continued)

(56) References Cited

U.S. PATENT DOCUMENTS 3,585,984 A  6/1971  Buchanan
4,763,648 A  8/1988  Wyatt
(Continued)

FOREIGN PATENT DOCUMENTS

CN  104111324 A  10/2014
CN  204192629 U  3/2015
(Continued)

OTHER PUBLICATIONS

Ames et al., "An Appraisal of the "Vacutainer" System for Blood Collection", Annals of Clinical Biochemistry: International Journal of Laboratory Medicine vol. 12 Issue: 1-6, pp. 151-155.
(Continued)

*Primary Examiner* — Benjamin R Schmitt
(74) *Attorney, Agent, or Firm* — Perkins Coie LLP

(57) ABSTRACT

The present technology is directed to extraction devices, systems, and methods for controllably withdrawing and transferring fluid samples, such as blood, from a sample collection container to a testing device. For example, some embodiments of the present technology provide fluid extraction devices that include a fluid control module, a housing containing a receiving element and a suction element, and an actuator. To transfer blood from a sample collection container to a testing device, a user places the sample collection container over the receiving element and inserts the testing device into an outlet of the fluid control module. The user then pushes a lever or otherwise actuates the actuator, which automatically withdraws a predetermined volume of blood from the sample collection container and transfers it to the testing device positioned at the outlet of the fluid control module.

8 Claims, 8 Drawing Sheets

(51) Int. Cl.
*A61J 1/20* (2006.01)
*A61J 1/22* (2006.01)
*B01L 3/02* (2006.01)
*G01N 1/00* (2006.01)
*A61B 5/15* (2006.01)
*A61B 10/00* (2006.01)
*A61J 1/14* (2023.01)

(52) U.S. Cl.
CPC .......... *G01N 1/14* (2013.01); *A61B 5/150236* (2013.01); *A61B 5/150251* (2013.01); *A61B 5/150755* (2013.01); *A61B 10/0045* (2013.01); *A61J 1/14* (2013.01); *B01L 3/0224* (2013.01); *B01L 2400/0478* (2013.01); *G01N 35/1009* (2013.01); *G01N 2001/002* (2013.01); *G01N 2001/1418* (2013.01); *G01N 2035/1023* (2013.01); *G01N 2035/1027* (2013.01)

(58) Field of Classification Search
CPC ... G01N 2001/1418; G01N 2035/1023; G01N 2035/1027; A61B 5/150236; A61B 5/150251; A61B 5/150755; A61B 10/0045; A61J 1/20; A61J 1/2096; A61J 1/22; A61J 1/14; B01L 3/0224; B01L 2400/0478
See application file for complete search history.

(56) References Cited

U.S. PATENT DOCUMENTS

| | | |
|---|---|---|
| 5,143,084 A | 9/1992 | Macemon et al. |
| 5,270,219 A | 12/1993 | Decastro et al. |
| 5,286,453 A | 2/1994 | Pope |
| 5,624,849 A | 4/1997 | Thomas et al. |
| 5,653,686 A | 8/1997 | Coulter et al. |
| 5,893,397 A | 4/1999 | Peterson et al. |
| 7,011,742 B2 | 3/2006 | Rosiello |
| 7,771,383 B2 | 8/2010 | Truitt et al. |
| 2006/0051252 A1* | 3/2006 | Yuan ................ B01L 3/0217 422/400 |
| 2014/0039348 A1* | 2/2014 | Bullington ........ A61B 10/0096 422/546 |
| 2017/0246623 A1 | 8/2017 | Magnusson |
| 2017/0274376 A1* | 9/2017 | Nobile ................ G01N 1/4077 |
| 2019/0159710 A1 | 5/2019 | Iwasawa et al. |
| 2019/0274609 A1 | 9/2019 | Wilkinson et al. |

FOREIGN PATENT DOCUMENTS

| | | |
|---|---|---|
| MX | 2015014483 A | 2/2016 |
| MX | 2018001352 A | 5/2018 |

OTHER PUBLICATIONS

Bush et al., "The Evolution of Evacuated Blood Collection Tubes." LabNotes, vol. 19, No. 1, 2009.

Lach et al., "An assessment of some hazards associated with the collection of venous blood", Journal of Hospital Infection vol. 4 Iss. 1, pp. 57-63.

Sara Pruett, "Needle-Stick Safety for Phlebotomists", Laboratory Medicine vol. 29 Iss. 12, pp. 754 760.

* cited by examiner

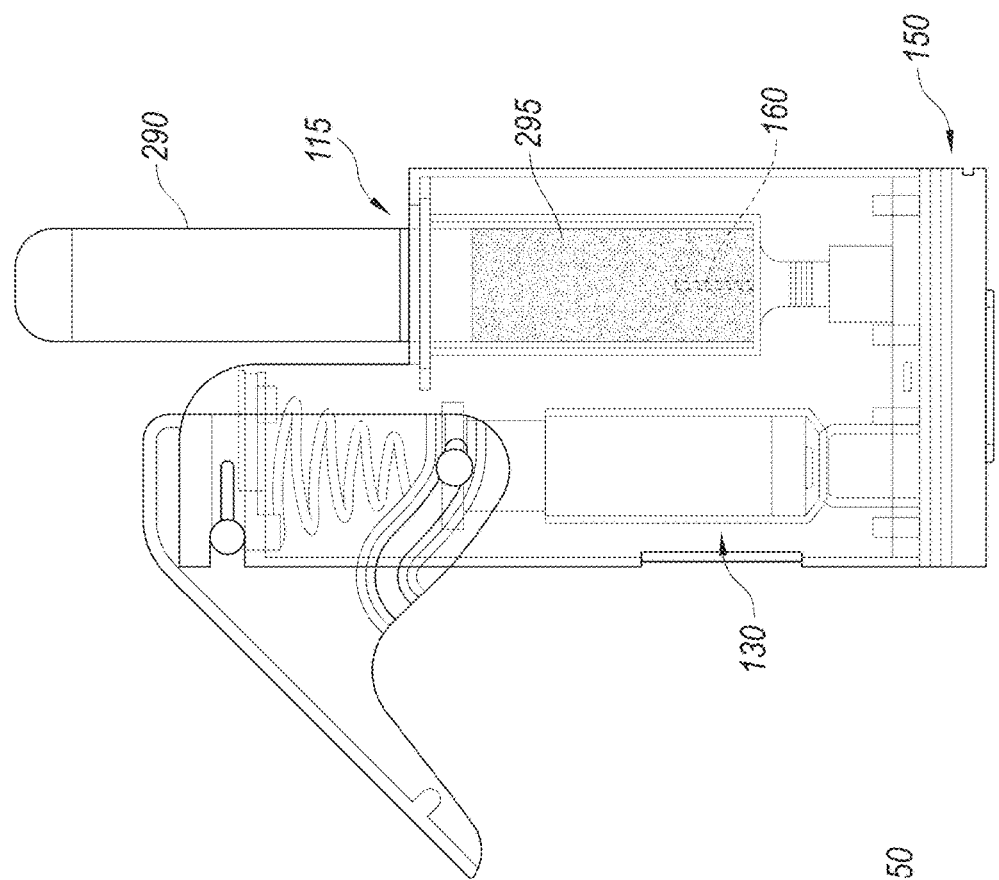
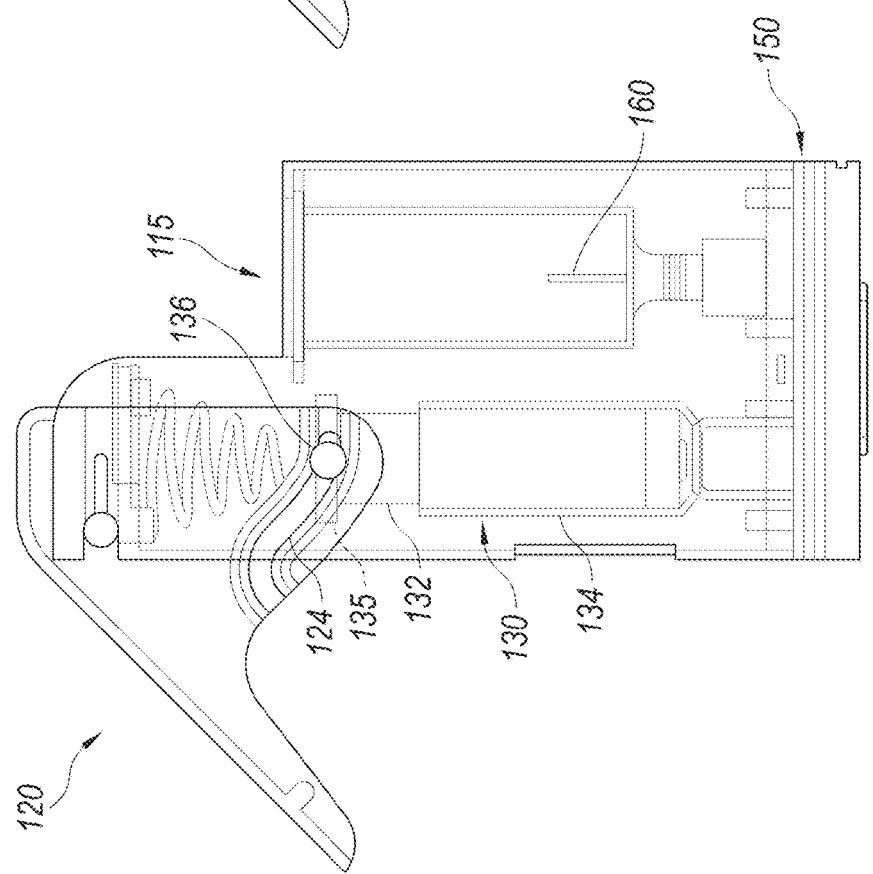
Fig. 2A
Fig. 2B

SELF-CONTAINED SYSTEMS AND METHODS FOR CONTROLLED DISPENSING OF HAZARDOUS FLUID

CROSS-REFERENCE TO RELATED APPLICATION(S)

The present application claims priority to U.S. Provisional Patent Application No. 62/856,382, filed Jun. 3, 2019, the disclosure of which is incorporated by reference in its entirety.

STATEMENT REGARDING FEDERALLY SPONSORED RESEARCH

This invention was made with government support under Grant No. HDTRA1-16-C-0029, awarded by the Defense Threat Reduction Agency. The government has certain rights in the invention.

TECHNICAL FIELD

The present technology is directed to systems, devices, and methods for dispensing hazardous fluid and, in particular, to systems, devices, and methods for transferring a predetermined volume of a biological fluid from a sample collection container to another device.

BACKGROUND

Biological fluid samples, such as blood samples, are frequently used to diagnose disease. Blood samples can be collected through a variety of procedures. For example, when only a relatively small volume of blood is needed, a healthcare professional or other user can use a lancet to prick a patient's finger. When relatively larger volumes of blood are needed, the healthcare professional or other user may need to withdraw blood through venipuncture and vacutainer or syringe extraction. In addition to facilitating extraction of relatively larger volumes of blood, vacutainers can also serve as a reservoir for the blood once it is withdrawn. Blood can then be selectively withdrawn from the vacutainer to use with diagnostic or other tests. However, removing blood from a vacutainer presents health hazards to the user, particularly when the vacutainer contains a blood sample of patients infected with deadly and/or contagious pathogens, such as Ebola. Even when performed by trained healthcare professionals, removing blood from a vacutainer involves risks associated with spilling the sample, aerosolizing pathogens contained within the sample, contaminating gloves or clothes with residue on the cap or pipette tip, and/or accidental puncture and subsequent infection.

BRIEF DESCRIPTION OF THE DRAWINGS

Many aspects of the present technology can be better understood with reference to the following drawings. The components in the drawings are not necessarily to scale, and instead emphasis is placed on illustrating clearly the principles of the present disclosure.

FIGS. 2A-2D illustrate a workflow for withdrawing a biological fluid from a sample collection container using the extraction device shown in FIGS. 1A-1C and configured in accordance with embodiments of the present technology.

DETAILED DESCRIPTION

Figure 1A:
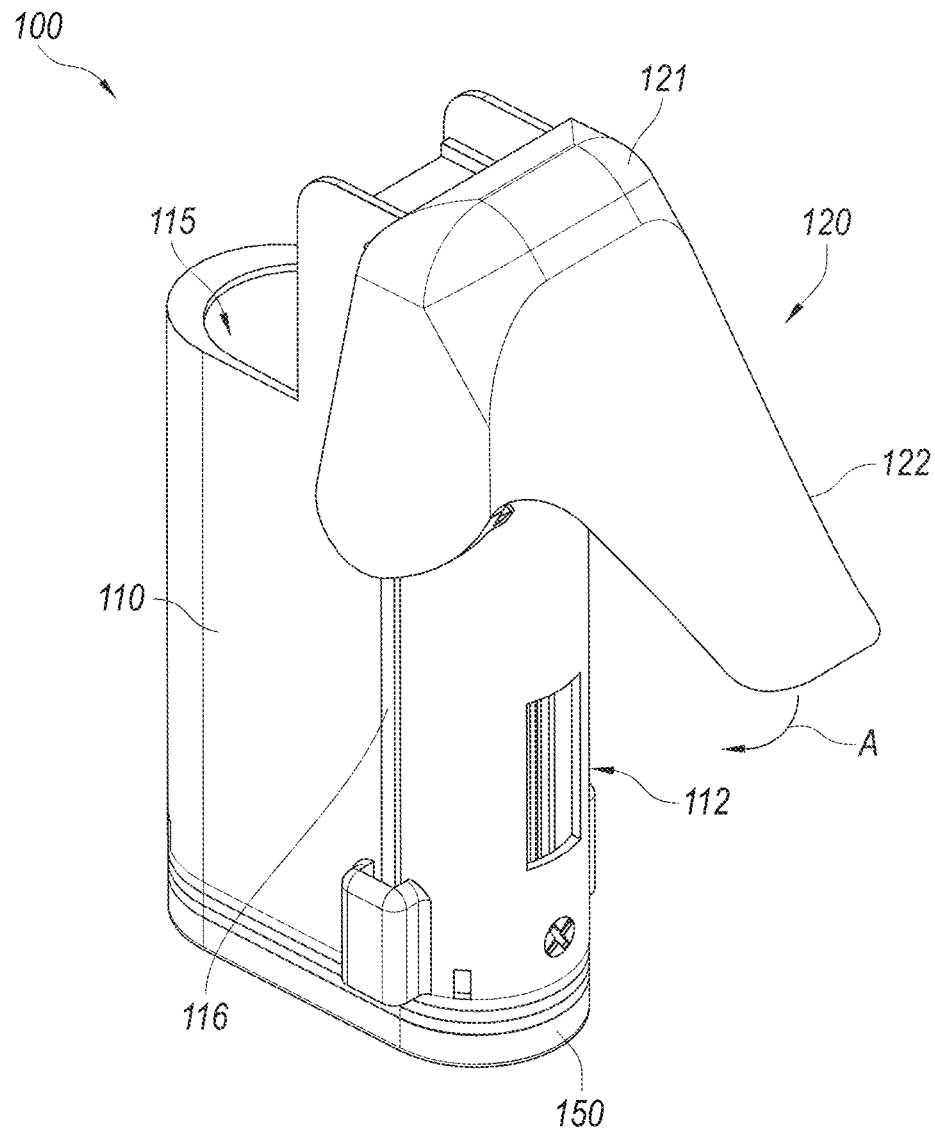
FIG. 1A is an isometric view of an extraction device configured in accordance with embodiments of the present technology.

The present technology is directed to extraction devices, systems, and methods for controllably withdrawing and transferring fluid samples, such as blood, from a sample collection container to a testing device. Healthcare professionals commonly collect blood and other fluid samples from patients to aid in the diagnosis, screening, monitoring, and/or treatment of various diseases. To withdraw a blood sample from a patient, a health professional typically inserts a needle into the patient's blood vessel and withdraws blood using a syringe and/or vacutainer. The blood sample is stored in the vacutainer until it can be transferred to the desired testing device. Conventional techniques for transferring blood from the vacutainer to the testing device include removing the vacutainer cap and withdrawing the blood using a pipette and/or inserting a needle connected to a syringe through the vacutainer cap and withdrawing blood through the needle. However, these conventional techniques have several disadvantages. For example, these techniques may risk exposing the user to pathogens contained in the blood sample, such as through spilling of the blood sample, aerosolization of pathogens contained in the blood sample, contamination of gloves or clothing, accidental puncture with the needle, or other means. Furthermore, in part because of the foregoing risks, these techniques are typically only performed by trained healthcare professionals, which can increase the time between when blood is drawn from the patient and when the blood sample is actually tested, which decreases the use of rapid diagnostic tests in point-of-care settings. Yet another potential disadvantage of many conventional techniques is that, if done improperly, such techniques may contaminate the blood sample and affect the accuracy of tests performed using the blood sample.

The devices, systems, and methods described herein are expected to address some or all of the foregoing limitations of previous techniques for withdrawing biological fluid from a sample collection container (e.g., a vacutainer). For example, the present technology provides fluid extraction devices including a fluid control module, an actuator, and a receiving element in fluid communication with the fluid control module. To transfer blood from a vacutainer to a testing device, a user simply inserts the testing device into the outlet of the fluid control module and, without removing the cap, inserts the vacutainer into/over the receiving element. The user then pushes a lever or otherwise actuates the actuator, which automatically withdraws a predetermined volume of blood from the vacutainer and transfers it to the testing device positioned at the outlet of the fluid control module. Accordingly, in at least some embodiments, the extraction devices described herein are self-contained, controlled, and/or consistent in dispensing suitable, metered volumes of blood or other fluid for testing, while reducing the risk of the user being exposed to hazardous contents contained within the fluid. For example, the devices enable a user to transfer relatively large volumes of blood (e.g., 1 mL) to a test device without removing a vacutainer cap or using an exposed needle, which is expected to reduce the risk of spillage, accidental puncture, contamination, and the like.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims but are not described in detail with respect to FIGS. 1A-3D.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%. In instances in which relative terminology is used in reference to something that does not include a numerical value, the terms are given their ordinary meaning to one skilled in the art.

Figure 1B:
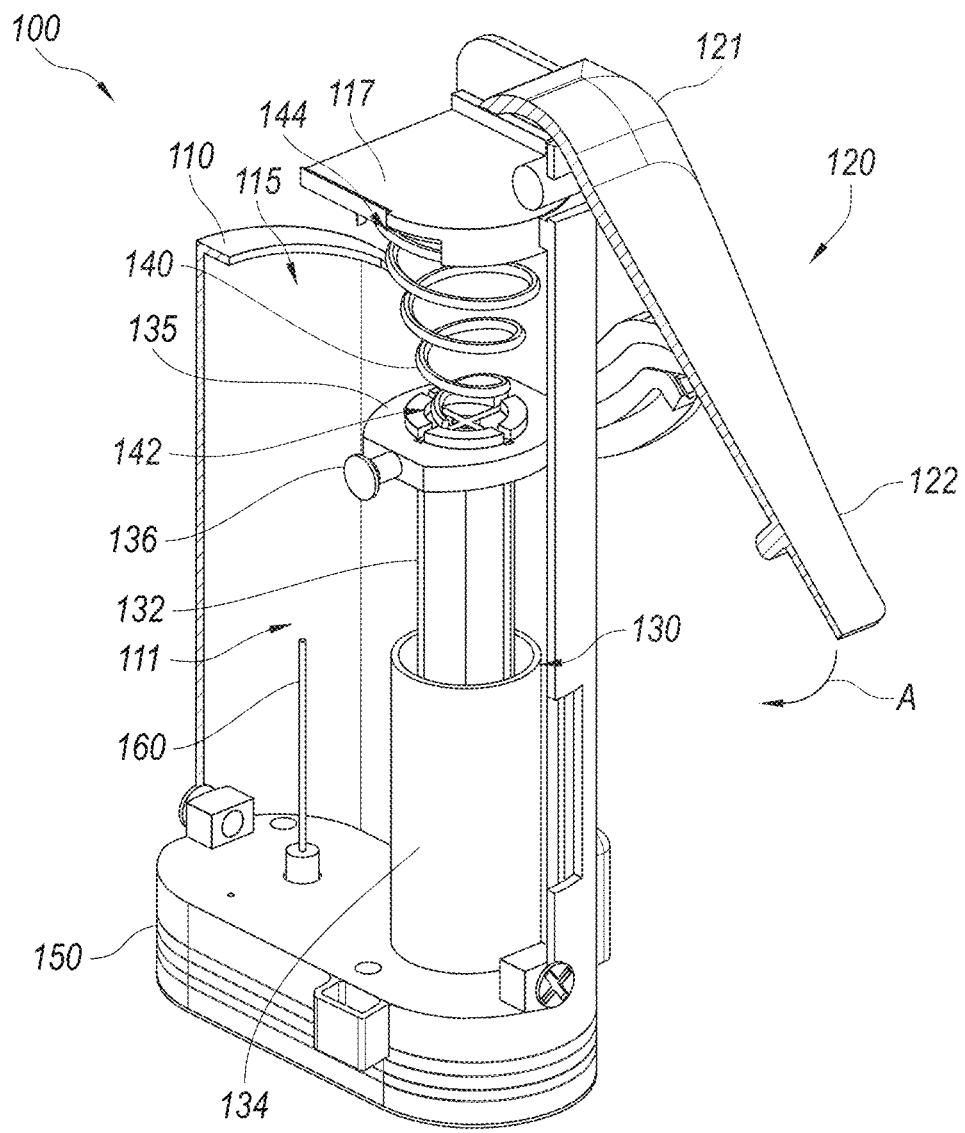
FIG. 1B is a partially cut-away view of the extraction device shown in FIG. 1A and configured in accordance with embodiments of the present technology.
Figure 1C:
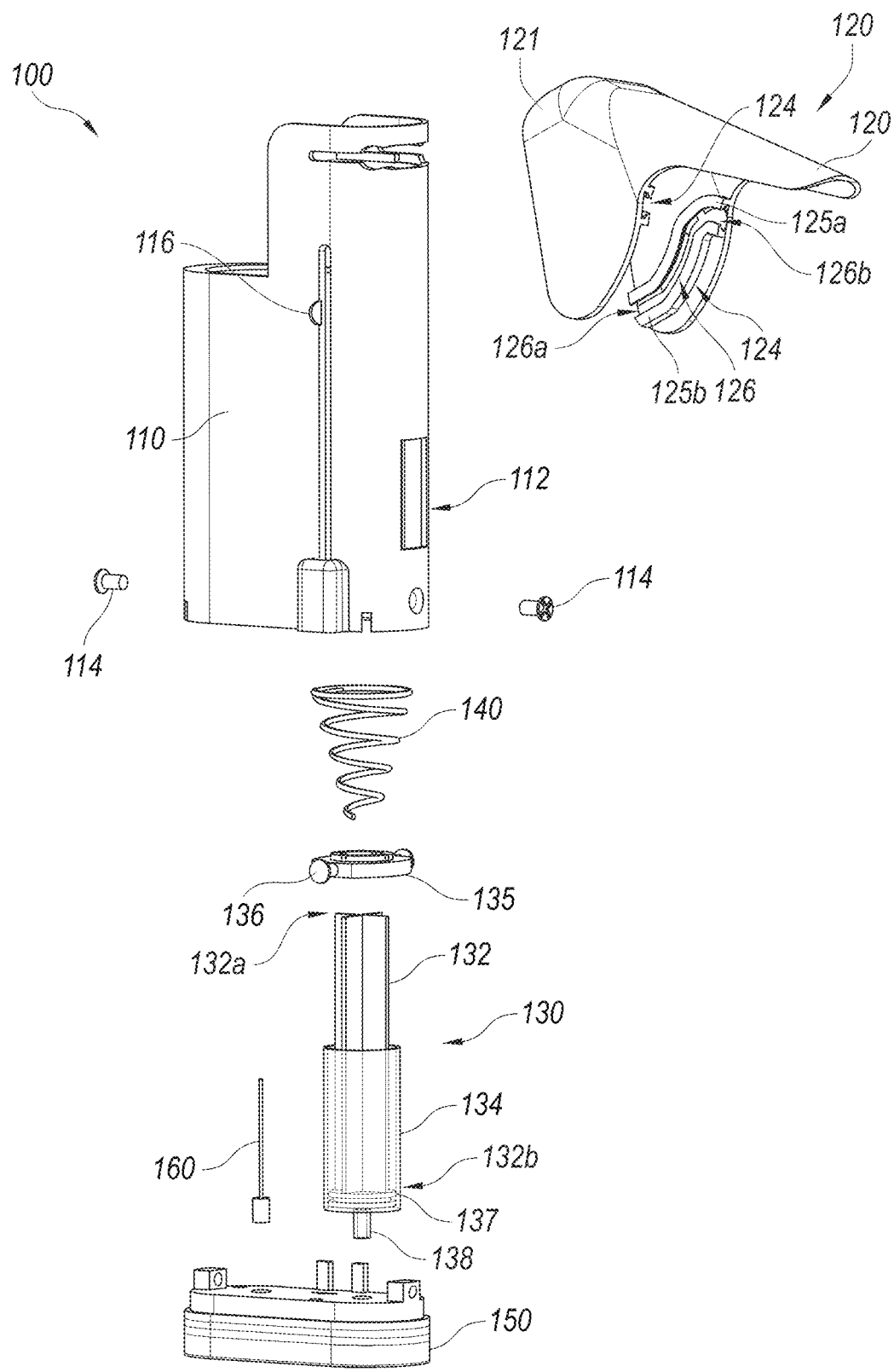
FIG. 1C is an exploded view of the extraction device shown in FIGS. 1A and 1B and configured in accordance with embodiments of the present technology.

As described previously, the present technology is directed to extraction devices, systems, and methods for withdrawing fluid samples, such as blood, from a sample collection container. FIGS. 1A-1C, for example, illustrate a fluid extraction system/device 100 (the "device 100") configured in accordance with select embodiments of the present technology. More specifically, FIG. 1A is an isometric view of the device 100, FIG. 1B is a partially cut-away isometric view of the device 100, and FIG. 1C is an exploded view of the device 100. As described in greater detail below, the device 100 is configured to withdraw a predetermined amount of fluid contained within a sample collection container, such as a vacutainer. The device 100 is further configured to transfer the withdrawn fluid to an outlet of the device 100. A test device (e.g., a lateral flow diagnostic device) can be positioned at the outlet to receive the withdrawn fluid.

Referring first to FIGS. 1A-1C collectively, the device 100 includes a body element or housing 110 coupled to a fluid control module 150. The housing 110 forms an external surface of the device 100 and defines a chamber 111 therein (FIG. 1B). The chamber 111 can contain various components of the device 100, including, for example, a receiving element 160, a suction element 130, and a spring element 140. The receiving element 160, shown in FIGS. 1B and 1C, is configured to engage a sample collection container (e.g., a vacutainer, a vial, or the like—not shown) and enable fluid contained within the sample collection container to be withdrawn therefrom. For example, in some embodiments a portion of the receiving element 160 is placed in fluid communication with an interior of the sample collection container when the sample collection container engages the receiving element 160. In some embodiments, the receiving element 160 is a puncture element (e.g., a needle), although other suitable receiving elements designed to interface with or otherwise engage a sample collection container can be used. Because the receiving element 160 is within the housing 110, a user is generally not exposed to the receiving element 160 during operation of the device 100.

As best shown in FIG. 1A, the housing 110 includes a port 115. As described in greater detail with respect to FIGS. 2A-2D, a user can insert a vacutainer or other sample collection container (not shown) into the chamber 111 via the port 115. The port 115 can be oriented such that a sample collection container inserted through the port 115 aligns with and can be advanced over the receiving element 160. For example, in embodiments in which the sample collection container is a vacutainer and the receiving element 160 is a needle, the port 115 may be sized and shaped to direct the vacutainer toward the needle such that a cap on the vacutainer is pierced by the needle to place the needle in fluid communication with an interior of the vacutainer. In some embodiments, the housing 110 may also include a channel or other track (not shown) extending at least partially between the port 115 and the receiving element 160 to ensure a sample collection container inserted into the chamber 111 via the port 115 is directed toward and/or onto the receiving element 160. In some embodiments, the device 100 optionally includes a cover or lid (not shown) positioned over the port 115 when the device 100 is not in use. The cover or lid can then be opened or otherwise removed before a user inserts a sample collection container into the device 100.

The housing 110 can include a number of other features, such as a slit 116, an opening 112, and a reaction surface 117. The slit 116 can be an elongated opening that extends generally vertically along a portion of the housing 110. As described in detail below, the slit 116 enables various components (e.g., appendages 136 on the suction element 130, described below) to extend outside the chamber 111 and move relative to the housing 110. The housing 110 can also optionally include the opening 112, which is a window to permit a user to see into the chamber 111. In the illustrated embodiment, the opening 112 is generally rectangle-shaped, although the opening 112 can take other suitable shapes, such as circular, elliptical, or the like. The opening 112 may optionally include a transparent covering (e.g., plastic, plexiglass, glass, etc.) that fluidly isolates the chamber 111 from the exterior environment at the opening 112, but that still enables a user to see into the chamber 111. The reaction surface 117 (best shown in FIG. 2B) can be any portion of the housing 110 or other structure that remains static relative to the housing 110 and/or fluid control module 150 during actuation of the device 100.

As noted above and as best seen in FIGS. 1B and 1C, the device 100 further includes a suction element 130. The suction element 130 can be a syringe, pump, vacuum, or other feature for moving fluid. In the illustrated embodiment, for example, the suction element 130 is a syringe having a barrel 134 and a plunger 132. The barrel 134 can be a casing, tube, cylinder, container, or the like. In at least some configurations, the barrel 134 is configured to hold a fluid. A distal end portion of the barrel 134 can also include a tip element 138 (e.g., an adapter). The tip element 138 can include an inner lumen fluidly coupled to the barrel 134 such that fluid received in the tip element 138 can be routed into the barrel 134. The barrel 134 can be secured to the fluid control module 150, the housing 110, or another generally static feature on the device 100 such that it does not move relative to the fluid control module 150 or the housing 110 when the device 100 is actuated, as described in detail below.

The plunger 132 can be an elongated shaft, rod, or the like having a first portion (e.g., a proximal end portion 132a) and a second portion (e.g., a distal end portion 132b). The proximal end portion 132a includes or is secured to a cap 135 having one or more appendages 136 (e.g., knobs, hooks, balls, or the like). As illustrated, the cap 135 can be flanged or otherwise provide a generally larger surface area than a cross-section taken along the shaft of the plunger 132. The appendages 136 can extend through the slit 116 in the housing 110. As described in detail below, the appendages 136 can releasably engage an actuator (e.g., actuator 120) that drives operation of the suction element 130. Although illustrated as having two appendages 136, the device 100 can have more or fewer appendages, such as one, three, four, or more. The distal end portion 132b of the plunger 132 fits within the barrel 134 and forms a pneumatic seal therebetween (e.g., via the seal 137).

At least a portion of the plunger 132 is moveable relative to the barrel 134. For example, the plunger 132 can move further into and further out of barrel 134, depending on whether it is "pushed" or "pulled." As described in detail with respect to FIGS. 2A-2D, pulling the plunger 132 further out of the barrel 134 creates a negative pressure in the barrel 134 while generally increasing an interior volume of the barrel 134 between the tip element 138 and the seal 137. This can draw fluid into the barrel 134 via the tip element 138. In contrast, pushing the plunger 132 further into the barrel 134 creates a positive pressure in the barrel 134 while generally decreasing the interior volume of the barrel 134 between the tip element 138 and the seal 137. This can expel fluid contained within the barrel 134 via the tip element 138. The suction element 130 can therefore be transitioned between a plurality of states (e.g., positions, configurations, etc.) corresponding to how far the plunger 132 is inserted into the barrel 134. For example, in FIG. 1B, the suction element is shown in a first, generally "unloaded" state. The suction element is transitionable to a second, generally "loaded" state by withdrawing at least a portion of the plunger 132 from the barrel 134. As described in detail below, the suction element 130 is generally in the first state before the actuator 120 is actuated, and moves toward the second state when the actuator 120 is actuated to draw fluid out of a sample collection container and into the device 100.

As noted above, the device 100 further includes a spring element 140. As best shown in FIG. 1B, the spring element 140 extends between the suction element 130 and the reaction surface 117. For example, a first end portion 142 of the spring element 140 is coupled to or otherwise interfaces with the cap 135 of the suction element 130. A second end portion 144 of the spring element 140 is coupled to or otherwise interfaces with the reaction surface 117. The spring element 140 can be composed of any suitable material, such as steel (e.g., stainless steel) or the like. The spring element 140 is compressed when the suction element 130 moves from the first state toward the second state (e.g., as the plunger 132 is withdrawn from the barrel 134). As described in detail below, the force stored within the spring element 140 as the suction element moves from the first state toward the second state is subsequently used to move the suction element 130 from the second state back toward the first state.

As indicated above, the device 100 can further include an actuator 120. In the illustrated embodiment, the actuator 120 includes a rotatable feature 121 and a lever or handle 122 extending from the rotatable feature 121. The rotatable feature 121 can be a lid, cap, cover, arm, or other component that is pivotably and/or rotatably coupled to the housing 110.

In the illustrated embodiment, for example, the rotatable feature 121 is coupled to a portion (e.g., an upper portion) of the housing 110 spaced apart from the fluid control module 150, although in other embodiments the rotatable feature 121 can be coupled to another portion of the housing 110. The actuator 120 can be coupled to the housing 110 via any suitable connection feature (not shown). For example, the connection feature can be a cylindrical body that can engage with (e.g., snap onto) a corresponding feature of the housing 110. In other embodiments, the connection feature can take other suitable configurations that enable the rotatable feature 121 to pivot, rotate, or otherwise move relative to the housing 110 when the actuator 120 is coupled to the housing 110.

As best seen in FIG. 1C, which shows the actuator 120 rotated upward to better show various features, the actuator 120 further includes one or more features that engage (and/or are configured to engage) a portion of the suction element 130. For example, the actuator 120 can include one or more tracks 124. The tracks 124 are configured to receive the appendages 136 on the suction element 130 to releasably couple the suction element 130 to the actuator 120. The tracks 124 may also be sized and shaped to constrain the movement of the one more appendages 136 to a predetermined route during actuation of the device 100. For example, each track 124 can include a first rail 125a (e.g. an upper rail) and a second rail 125b (e.g., a lower rail). An elongated cavity or recess 126 is defined between the first rail 125a and the second rail 125b and extends between a first (e.g., proximal) end portion 126a and a second (e.g., distal) end portion 126b. In some embodiments, the first rail 125a and/or the second rail 125b include a flange or other feature for constraining movement of the appendages 136 along a length of the elongated cavity 126. As described below, the tracks 124 direct the appendages 136 to move through the elongated cavity 126 from the proximal end portion 126a toward the distal end portion 126b as the actuator 120 is actuated (e.g., as the lever 122 is pressed toward the housing 110 and the rotatable feature 121 rotates relative to the housing 110). Although illustrated has having two tracks 124, the actuator 120 can have more or fewer tracks, such as one, three, four, or more.

The actuator 120 is shown in FIGS. 1A and 1B in a pre-actuated configuration. The actuator 120 can be actuated by pressing, compressing, or otherwise moving the lever 122 toward the housing 110 (as shown by arrow A in FIGS. 1A and 1B). In other embodiments, the actuator 120 can be automatically actuated in response to a user input and/or action, such as pressing a button or flipping a switch (not shown). Because the actuator 120 is coupled to the suction element 130, actuation of the actuator 120 induces a corresponding movement in the suction element 130. More specifically, actuation of the actuator 120 initially transitions the suction element 130 from the first state toward the second state. For example, as the lever 122 on the actuator 120 is pressed toward the housing 110, the rotatable feature 121 rotates relative to the housing 110 and the appendages 136 on the suction element 130 move through the elongated cavity 126 from the proximal end portion 126a toward the distal end portion 126b. The tracks 124 on the actuator 120 are oriented such that movement of the appendages 136 from the proximal end portion 126a toward the distal end portion 126b generates a generally upward force on the plunger 132 and withdraws the plunger 132 from the barrel 134 (e.g., transitioning the suction element 130 toward the second state). As previously described, withdrawing the plunger 132 from the barrel 134 also compresses the spring element 140 between the cap 135 of the suction element 130 and the reaction surface 117. However, the engagement between the appendages 136 and the tracks 124 prevents the spring element 140 from pushing the plunger 132 back into the barrel 134 while the appendages 136 are in the elongated cavity 126. Accordingly, when the appendages 136 reach the distal end portion 126b of the elongated cavity 126, the suction element 130 is in and/or near the second state.

Once the appendages 136 reach the distal end portion 126b of the elongated cavity 126, the suction element 130 transitions from the second state back toward the first state (e.g., the plunger 132 is pushed back into the barrel 134). More specifically, once the appendages 136 are in the distal end portion 326b of the elongated cavity 126, the appendages 136 are no longer constrained by the tracks 124. Therefore, the force in the compressed spring element 140 causes the spring element 140 to expand and push the plunger 132 back into the barrel 134, transitioning the suction element 130 from the second state back toward the first state. Accordingly, the net effect of actuating the actuator 120 is moving the suction element 130 from the first state to the second state, and from the second state back to the first state. In the illustrated embodiment, this transition occurs automatically when the lever 122 is pressed toward the housing 110. Although described as having a rotatable feature 121 and a lever 122, the actuator 120 can take other suitable forms. For example, the actuator 120 can have any suitable form configured to engage with and move a portion of the suction element 130 when the actuator 120 is actuated.

As noted above, the device can further include a fluid control module 150. The fluid control module 150 can interface with the suction element 130 and the receiving element 160 and be configured to route fluid therebetween during actuation of the actuator 120. For example, the receiving element 160 may be inserted into a corresponding first port (e.g., first port 352, shown in FIG. 3B) on the fluid control module 150, and the tip element 138 of the suction element 130 may be inserted into a corresponding second port (e.g., second port 354, shown in FIG. 3B) on the fluid control module 150. As described in greater detail with respect to FIGS. 3A-3D, the fluid control module 150 further includes a valve system for controlling the flow of fluid between, among other things, the receiving element 160 and the suction element 130. The fluid control module 150 can also include an outlet (e.g., outlet 358, shown in FIGS. 3C and 3D) for transferring fluid to a test device. In some embodiments, the fluid control module 150 can also provide a support or foundation for the device 100. For example, the fluid control module 150 may have a generally flat bottom surface for supporting the device 100 in an upright position. Accordingly, the fluid control module 150 can also be referred to as a "base element." The fluid control module 150 can be secured to the housing 110 via one or more fasteners 114 (e.g., threaded screws or the like) and/or via other suitable fastening techniques, such as gluing, welding, or the like. Additional details of the fluid control module 150 are described with respect to FIGS. 3A-3D.

Figure 2D:
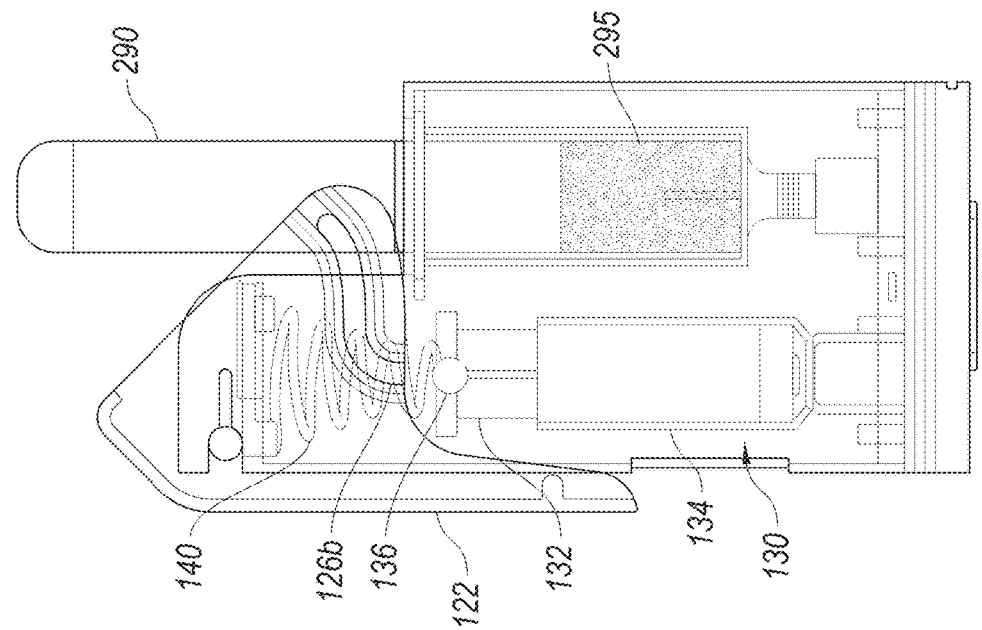

FIGS. 2A-2D illustrate various stages of a workflow for using the device 100 to transfer fluid from a sample collection container 290 to a test device (not shown). FIG. 2A illustrates the device 100 before the sample collection container 290 is inserted into the device 100. As illustrated, the suction element 130 is in the first (e.g., unloaded) state and the actuator 120 is in a pre-actuated configuration. Referring next to FIG. 2B, a user can load a sample collection container 290 holding a biological fluid sample 295 (e.g., blood) into the device 100. For example, the user can insert the sample collection container 290 into the port 115 and advance the sample collection container over the receiving element 160. In some embodiments, the sample collection container 290 is a vacutainer and the receiving element 160 is a needle that punctures the cap or lid of the vacutainer. Excess pressure contained within the sample collection container 290 can be automatically purged and directed toward a waste chamber in the fluid control module 150, described in detail with respect to FIGS. 3C and 3D. In some embodiments, once the sample collection container 290 is inserted into the device 100, the user does not need to further touch or otherwise handle the sample collection container 290 to withdraw fluid from the sample collection container 290 and transfer it to a test device.

Figure 2C:
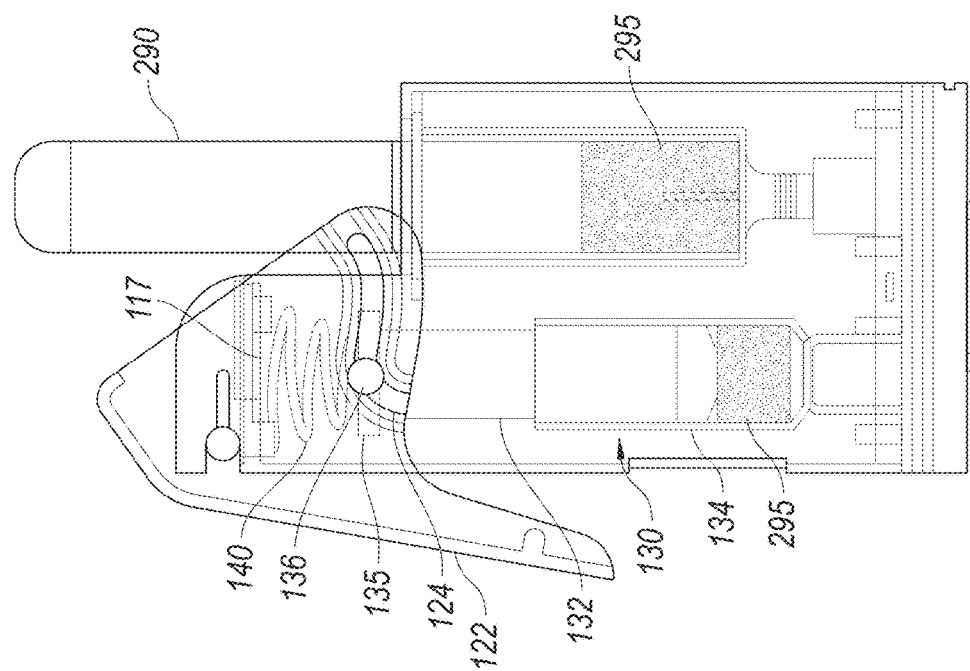

To withdraw a portion of the fluid sample 295 from the sample collection container 290, a user actuates the actuator 120, such as by pressing the lever 122 toward the housing 110 (e.g., transitioning from the configuration shown in FIG. 2B to the configuration shown in FIG. 2D). Referring to FIG. 2C, which illustrates an intermediate stage as the lever 122 is being pressed toward the housing 110, pressing the lever 122 toward the housing causes the appendages 136 to move through the tracks 124 and withdraws the plunger 132 from the barrel 134, transitioning the suction element 130 from the first state toward the second state. The negative pressure generated by withdrawing the plunger 132 from the barrel 134 withdraws at least a portion of the fluid sample 295 from the sample collection container 290 and routes the withdrawn portion of the fluid sample 295 toward and/or into the suction element 130. As the plunger 132 is withdrawn, the spring element 140 is also compressed between the cap 135 of the suction element 130 and the reaction surface 117.

Referring now to FIG. 2D, as the actuator 120 is further pressed toward the housing 110 (and/or as the rotatable feature 121 reaches a specified rotation angle relative to the housing 110), the appendages 136 align with and/or exit the distal end portion 126b of the track 124 and are thus no longer constrained by the tracks 124. The spring element 140, which was compressed as the lever 122 was being pushed toward the housing 110, pushes the plunger 132 back into the barrel 134, transitioning the suction element 130 from the second state back toward the first state. The positive pressure generated by pushing the plunger 132 back into the barrel 134 expels the portion of the fluid sample 295 previously drawn into the suction element 130. The expelled portion of fluid sample 295 is routed to an outlet of the device 100 via the fluid control module 150. At any stage of operation, a user can position a test device or a portion of a test device (not shown) inside, at, and/or proximate the outlet for receiving the expelled portion of the fluid sample 295.

Once the device 100 has been actuated and the expelled portion of the fluid sample 295 has been transferred to the outlet 258, the device 100 can be automatically or manually transitioned back to the pre-actuated configuration. For example, in some embodiments a spring or other feature (not shown) may automatically push the lever 122 away from the housing 110 and toward the pre-actuated configuration. In other embodiments, a user may simply pull the lever 122 away from the housing 110 and toward the pre-actuated configuration. Regardless, placing the lever 122 in its pre-actuated configuration can reset the device 100 and enable the user to withdraw additional fluid sample 295 from the sample collection container 290, if desired. In some embodiments, a second sample collection container containing a different biological fluid sample can be inserted into the device 100 after the device 100 is reset.

The device 100 withdraws a predetermined and/or specific volume of fluid from the sample collection container 290 when actuated. For example, the volume of fluid is based at least in part on how far the plunger 132 is withdrawn from the barrel 134, which, in the illustrated embodiment, is determined in general by the configuration of the actuator 120, and in particular by the length, shape, and/or orientation of the track 324 on the actuator 120. Therefore, the actuator 120 can be associated with a predefined volume that will be transferred upon actuation of the device 100. In some embodiments, the device 100 may include multiple actuators 120, with each actuator corresponding to a predetermined and/or specific volume of fluid transfer. For example, a first actuator may induce transfer of 0.5 mL of fluid, a second actuator may induce transfer of 1.0 mL, and a third actuator may induce transfer of 1.5 mL of fluid. If a user wishes to change the volume of fluid transferred using the device, the user simply removes (e.g., snaps off) the actuator 120 from the device 100 and replaces it with (e.g., installs or snaps on) an actuator corresponding to the desired volume of fluid extraction. As one skilled in the art will appreciate, the device 100 can scaled in size to transfer any number of fluid volumes, such as those between about 0.1 mL to 100 mL. Without being bound by theory, one expected advantage of the present technology is that the device 100 can be designed to accommodate relatively large sample collection containers. Because the device 100 can be repeatedly actuated, the user may be able to perform multiple draws from a single relatively large sample collection container. This may further allow a healthcare professional to take a single relatively large blood draw from a patient (rather than multiple draws), and then, using the device 100, distribute the blood in portions to more than one test device for purpose-oriented testing.

Certain tests/test devices may require the biological fluid sample to be diluted or otherwise modified before being transferred to the test device. Accordingly, in some embodiments a buffer is stored/contained within the suction element 130. The buffer can be any suitable buffer for use with diagnostic or other tests. In some embodiments, the buffer is dehydrated. In other embodiments, the buffer is a fluid. When a sample collection container containing a fluid sample is loaded into the device 100 and the device 100 is actuated, the portion of the fluid sample drawn into the suction element 130 mixes with the buffer. If the buffer is a dehydrated buffer, mixing with the fluid sample rehydrates the buffer. The mixed buffer and fluid sample can then be routed to the outlet (and thus to a test device) when the plunger 132 expels the fluid from the suction element 130. Pre-loading the buffer into the suction element 130 enables the fluid to be diluted or otherwise treated and transferred to the test device in a single step.

Figure 3A:
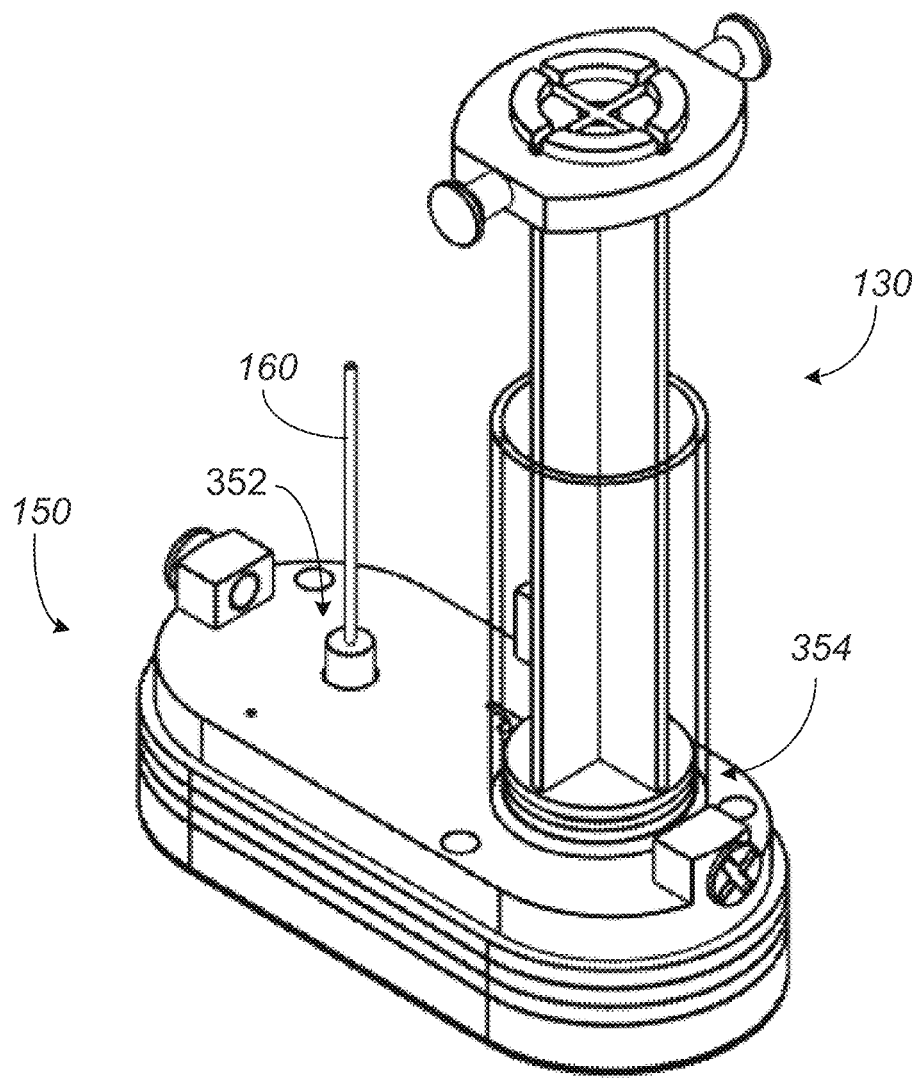
FIGS. 3A-3D illustrate additional features of a fluid control module of the extraction device shown in FIGS. 1A-1C and configured in accordance with embodiments of the present technology.
Figure 3B:
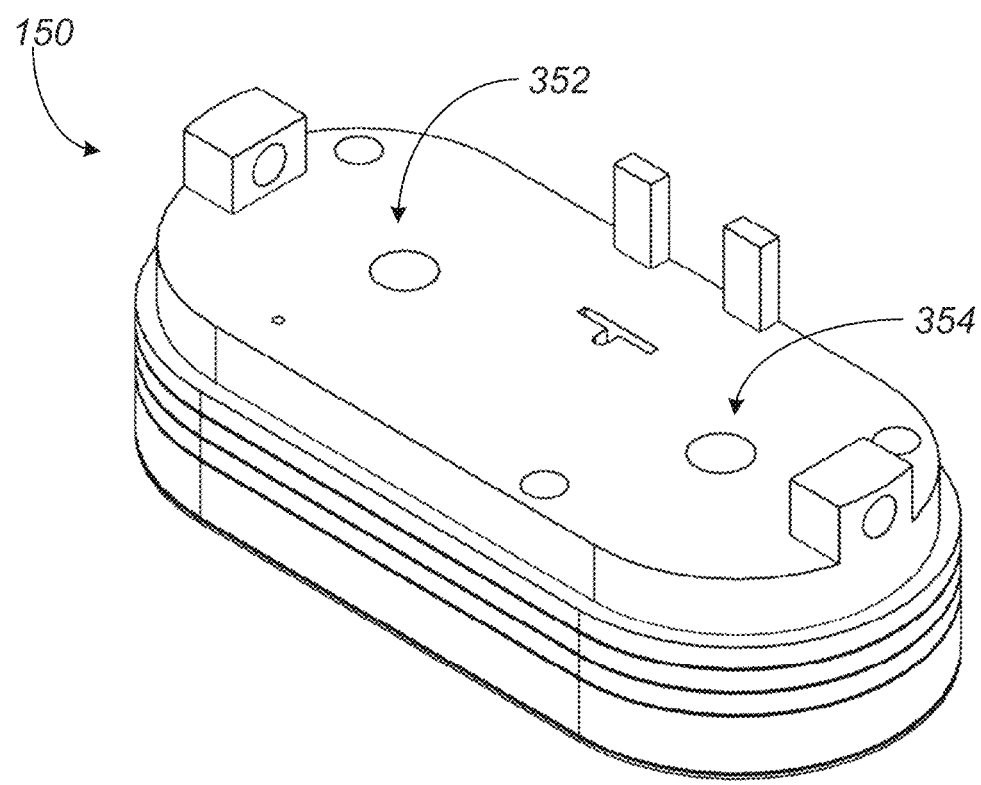
Figure 3C:
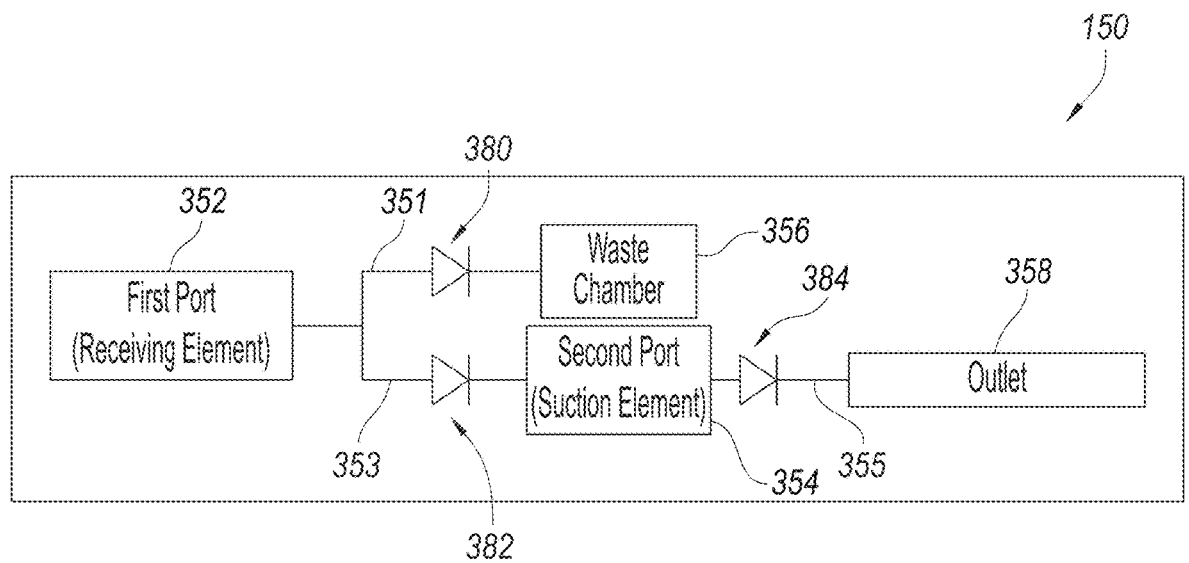
Figure 3D:
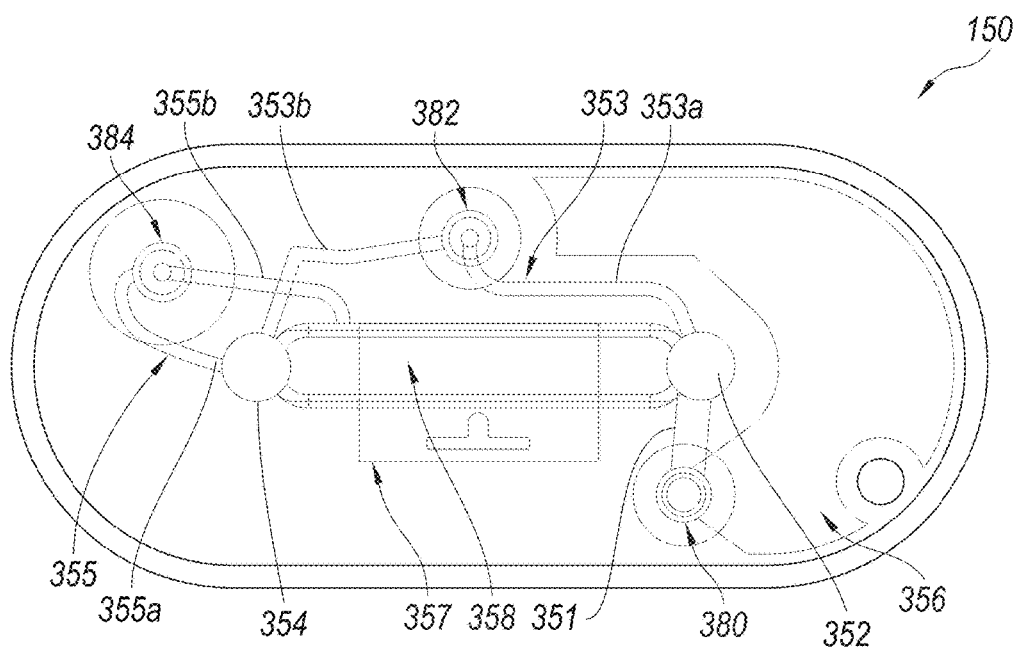

FIGS. 3A-3D illustrate additional details of the fluid control module 150 of the device 100. In particular, FIG. 3A is an isometric view of an exterior of the fluid control module 150 and shows the receiving element 160 and the suction element 130 coupled thereto. FIG. 3B is also an isometric view of the exterior of the fluid control module 150 with the receiving element 160 and the suction element 130 omitted. FIG. 3C is a schematic diagram of the fluid control module 150. FIG. 3D is a top-down partially schematic illustration of an interior of the fluid control module 150. Referring first to FIGS. 3A and 3B together, the fluid control module 150 includes a first port 352 and a second port 354. As illustrated, the first port 352 is configured to hold/dock the receiving element 160. Accordingly, the first port 352 can also be referred to as the receiving element port and/or an "inlet" to the fluid control module 150. The fluid control module 150 can be fluidically sealed to the receiving element 160 at the first port 152 via, for example, a Luer fitting, a compression ring, or the like. The second port 354 is configured to receive the tip element 138 (not shown in FIG. 3A) of the suction element 130. Accordingly, the second port 354 can also be referred to as the suction element port. The fluid control module 150 can be fluidically sealed to the suction element 130 at the second port 354 via, for example, a Luer fitting, a compression ring, or the like.

Referring next to FIGS. 3C and 3D, the fluid control module 150 further includes a waste chamber 356 and an outlet 358. The waste chamber 356 can be a reservoir contained within an interior of the fluid control module 150, and can be configured to receive the excess fluid and/or air that may escape a sample collection container when the sample collection container is advanced over the receiving element 160 (e.g., as shown in FIG. 2B). For example, it is known that vacutainers may have a positive pressure that can cause inadvertent air and/or fluid discharge when a needle is inserted through the cap. The fluid control module 150 ensures that any inadvertent discharge from a sample collection container is routed to the waste chamber 356 and does not affect the metered transfer of fluid. The outlet 358 is configured to receive fluid from the suction element 130 and transfer it to a diagnostic or other device. For example, the outlet 358 can comprise a cavity or other chamber. A test device (e.g., a diagnostic device) and/or a portion of a test device can be inserted into the cavity to receive a fluid sample therefrom. For example, in some embodiments the outlet 358 is sized and/or shaped to receive at least a portion of a lateral flow diagnostic device. The outlet 358 can further include a funnel (not shown) or other feature for directing the fluid sample onto/into an inlet or sample pad of the test device inserted into the outlet 358. In some embodiments, the fluid control module 150 can also include a fluid chamber 357 (FIG. 3D) positioned generally between the suction element 130 and the outlet 358. The fluid chamber 357 can receive fluid from the suction element 130 before it is routed to the outlet 358 to prevent pressurized release of the fluid from the outlet 358.

The first port 352, the second port 354, the waste chamber 356, and the outlet 358 can be fluidically coupled via one or more conduits. For example, the fluid control module 150 can include a first conduit or pathway 351 extending between and fluidically coupling the first port 352 and the waste chamber 356. Because the receiving element 160 is fluidically coupled to the fluid control module 150 at the first port 352 (FIG. 3A), the first conduit 351 also fluidically connects the receiving element 160 and the waste chamber 356. A first valve 380 can be positioned in the first conduit 351 to control the flow of fluid through the first conduit 351. In some embodiments, the first valve 380 is a one-way valve that enables fluid to flow from the receiving element 160 at the first port 352 to the waste chamber 356 while preventing fluid from flowing from the waste chamber 356 to the receiving element 160 at the first port 352.

The fluid control module 150 includes a second conduit or pathway 353 extending between and fluidically coupling the first port 352 and the second port 354. Because the receiving element 160 is fluidically coupled to the first port 352 and the suction element 130 is fluidically coupled to the second port 354 (FIG. 3A), the second conduit 351 also fluidically connects the receiving element 160 and the suction element 130. A second valve 382 can be positioned in the second conduit 353 to control the flow of fluid through the second conduit 353. In some embodiments, the second valve 382 is a one-way valve that enables fluid to flow from the receiving element 160 at the first port 352 to the suction element 130 at the second port 354 while preventing fluid from flowing from the suction element 130 at the second port 354 to the receiving element 160 at the first port 352. In some embodiments, such as illustrated in FIG. 3D, the second conduit 353 includes a second conduit first portion 353a and a second conduit second portion 353b. The second valve 382 is positioned within, on, and/or adjacent the second conduit 353 between the second conduit first portion 353a and the second conduit second portion 353b. However, as one skilled in the art will appreciate, the second valve 382 can be positioned at other positions along the second conduit 353 and still control the flow of fluid therethrough.

The fluid control module 150 further includes a third conduit or pathway 355 extending between and fluidically coupling the second port 354 and the outlet 358. Because the suction element 130 is fluidically coupled to the second port 354 (FIG. 3A), the third conduit 355 also fluidically connects the suction element 130 and the outlet 358. A third valve 384 can be positioned in the third conduit 355 to control the flow of fluid through the third conduit 355. In some embodiments, the third valve 255 is a one-way valve that enables fluid to flow from the suction element 130 at the second port 354 to the outlet 358 while preventing fluid from flowing from the outlet 358 to the suction element 130 at the second port 354. In some embodiments, such as illustrated in FIG. 3D, the third conduit 355 includes a third conduit first portion 355a and a third conduit second portion 355b. The third valve 384 is positioned within, on, and/or adjacent the third conduit 355 between the third conduit first portion 355a and the third conduit second portion 355b. However, as one skilled in the art will appreciate, the third valve 384 can be positioned at other positions along the third conduit 355 and still control the flow of fluid therethrough.

The first valve 380, the second valve 382, and the third valve 384 can be any suitable valve known in the art that can move between a first generally open position permitting fluid flow therethrough and a second generally closed position preventing fluid flow therethrough. For example, the first valve 380, the second valve 382, and/or the third valve 384 can be a rotary valve (e.g., a ball valve, a plug valve, a butterfly valve, etc.), a linear valve (e.g., a gate valve, a globe valve, a pinch valve, a diaphragm valve, a needle valve, a solenoid valve, etc.), a flap valve, or another suitable valve configured to selectively controlling the flow of fluid, such as for selectively permitting the flow of fluid in a first direction but not a second direction generally opposite the first direction. The first valve 380, the second valve 382, and the third valve 384 can be the same or different.

During operation of the device 100, the first valve 380, the second valve 382, and the third valve 384 selectively open and close to route fluid through the fluid control module 150. For example, before the actuator 120 is actuated (e.g., as shown in FIG. 2A), the first valve 380 is open and the second valve 382 is closed. When a user inserts a sample collection container over the receiving element 160 in the first port 352 (e.g., as shown in FIG. 2B), any fluid or air inadvertently discharged from the sample collection container is therefore routed toward the waste chamber 356 via the first conduit 351 rather than toward the suction element 130. By routing any inadvertent discharge into the waste chamber 356 rather than toward the suction element 130, the volume of fluid ultimately transferred when the device 100 is actuated remains generally unaffected by inadvertent discharge.

When the actuator 120 is actuated by pressing the lever 122 toward the housing 110 (e.g., as shown in FIG. 2C), the first valve 380 closes and the second valve 382 opens. As previously described, pressing the lever 122 toward the housing 110 withdraws the plunger 132 from the barrel 134, which generates a negative pressure in the suction element 130. Because the suction element 130 is fluidly coupled to the fluid control module 150 via the second port 354, the negative pressure induced by the suction element 130 at the second port 354 can close the first valve 380 and open the second valve 382. As described above, opening the second valve 382 fluidly couples the suction element 130 and the sample collection container at the receiving element 160, thereby enabling the negative pressure generated by the suction element 130 to withdraw fluid from the sample collection container (e.g., via the receiving element 160) and draw the fluids toward and into suction element 130 via the second conduit 353. Closing the first valve 380 fluidly isolates the waste chamber 356 from the suction element 130 and the sample collection container at the receiving element 160, thereby preventing or at least reducing the fluid in the waste chamber 356 from being drawn back toward the sample collection container and/or suction element 130 by the negative pressure via the first conduit 351.

Once the suction element 130 disengages from the actuator 120 and the plunger 132 is pushed back into the barrel 134 (e.g., as shown in FIG. 2D), the second valve 382 closes and the third valve 384 opens. Pressing the plunger 132 back into the barrel 134 generates a positive pressure in the suction element 130. Because the suction element 130 is fluidically coupled to the fluid control module 150 via the second port 354, the positive pressure generated by the suction element 130 can close the second valve 382 and open the third valve 384. As described above, opening the third valve 384 fluidly connects the suction element 130 and the outlet 358, thereby enabling the positive pressure to expel the fluid from the suction element 130 and direct it toward the outlet 358 via the third conduit 355. Closing the second valve 382 fluidly isolates the suction element 130 and the sample collection container, preventing or at least reducing the positive pressure from pushing fluid in the suction element 130 back toward the receiving element 160 via the second conduit 353.

In some embodiments, the valves 380, 382, and 384 automatically transition between the positions described above during actuation of the device 100. For example, as described above, the pressure differentials generated by movement of the suction element 130 can be sufficient to automatically control operation of the valves. In some embodiments, the fluid control module 150 may also include a controller or other component for actively driving movement of the valves to the described configurations.

As one skilled in the art will appreciate, even though many of the features of the devices are described herein as discrete components, one or more features can be combined or fused together without deviating from the scope of the present technology. The various components can be composed of any suitable material, such as plastics, metals, glass, or the like. Additionally, the device 100 can be manufactured through any suitable technique known in the art, including, for example, additive manufacturing processes (e.g., three-dimensional printing), subtractive manufacturing processes, injection molding, casting, or the like.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

I claim:

1. A system for controlled dispensing of biological fluid from a sample collection container, the system comprising:
a fluid control module having an inlet, an outlet, and one or more conduits for routing fluid between the inlet and the outlet;
a housing at least partially containing a receiving element and a suction element,
wherein—
the receiving element is in fluid communication with the fluid control module at the inlet and is configured to receive the sample collection container, and
the suction element is in fluid communication with the fluid control module between the inlet and the outlet; and
an actuator operably coupled to the suction element and configured to movably transition the suction element between a first state and a second state, wherein the actuator includes a lid having a plurality of tracks coupled to a portion for the suction element, the plurality of tracks being positioned to guide the suction element from the first state toward the second state when the lid is rotated relative to the housing,
and wherein—
moving the suction element from the first state toward the second state induces a negative pressure within at least a portion of the fluid control module to withdraw the biological fluid from the sample collection container and into the suction element, and
moving the suction element from the second state toward the first state induces a positive pressure within at least a portion of the fluid control module to expel the biological fluid from the suction element and toward the outlet.

2. The system of claim 1, further comprising a spring element configured to transition the suction element from the second state toward the first state.

3. The system of claim 1, wherein the suction element is a syringe having a barrel and a plunger, and wherein during operation—
as the suction element moves from the first state toward the second state, a portion of the plunger is withdrawn from the barrel, and
as the suction element moves from the second state toward the first state, the portion of the plunger is pushed back into the barrel.

4. The system of claim 1, wherein the suction element is configured to disengage from the plurality of tracks when the suction element reaches the second state.

5. The system of claim 4, further comprising a spring element coupled to the suction element, and wherein, during operation—
the spring element is compressed when the suction element moves from the first state toward the second state, and
the spring element is configured to transition the suction element from the second state back toward the first state when the suction element disengages from the plurality of tracks.

6. The system of claim 1, wherein the fluid control module comprises:
a waste chamber;
a first conduit extending between the inlet and the waste chamber;
a first one-way valve positioned along the first conduit, the first one-way valve configured to permit fluid to flow from the inlet to the waste chamber and to prevent fluid from flowing from the waste chamber to the inlet;
a second conduit extending between the inlet and the suction element;
a second one-way valve positioned along the second conduit, the second one-way valve configured to permit fluid to flow from the inlet to the suction element and to prevent fluid from flowing from the suction element to the inlet;
a third conduit extending between the suction element and the outlet; and
a third one-way valve positioned along the third conduit, wherein the third one-way valve is configured to permit fluid to flow from the suction element to the outlet and to prevent fluid from flowing from the outlet to the suction element.

7. The system of claim 6, wherein the first one-way valve is configured to close and the second one-way valve is configured to open when the suction element moves from the first state to the second state.

8. The system of claim 6, wherein the second one-way valve is configured to close and the third one-way valve is configured to open when the suction element moves from the second state to the first state.

* * * * *